United States Patent [19]

Eide et al.

[11] Patent Number: 5,396,894

[45] Date of Patent: Mar. 14, 1995

[54] DISPOSABLE PRESSURE CUFF FOR A BLOOD PRESSURE MONITOR

[76] Inventors: Mark E. M. Eide, 1810 Noah Dr., Corona, Calif. 90277; Michael D. Buren, 1111 North Olive, Santa Ana, Calif. 92703

[21] Appl. No.: 116,529

[22] Filed: Sep. 7, 1993

[51] Int. Cl.[6] .............................................. A61B 5/02
[52] U.S. Cl. .................................. 128/686; 606/202
[58] Field of Search ............................. 128/677–686; 606/201–204; 607/112

[56] References Cited

U.S. PATENT DOCUMENTS

| | | | |
|---|---|---|---|
| 3,570,495 | 3/1971 | Wright | 606/202 |
| 4,784,889 | 11/1988 | Daniels | 128/876 |
| 4,979,953 | 12/1990 | Spence | 128/686 |
| 5,038,797 | 8/1991 | Batters | 607/149 |
| 5,201,758 | 4/1993 | Glover | 128/686 |
| 5,219,356 | 6/1993 | Harreld et al. | 606/203 |
| 5,243,991 | 9/1993 | Marks | 128/686 |

*Primary Examiner*—Lee S. Cohen
*Assistant Examiner*—Robert L. Nasser, Jr.
*Attorney, Agent, or Firm*—Gary Appel

[57] ABSTRACT

A disposable blood pressure cuff for use in a conventional blood pressure measuring and/or monitoring system comprises an elongate, flexible, inflatable plastic sleeve sized to wrap around an individual's upper arm above the elbow, a flexible tube connected to the sleeve to enable the internal pressurization thereof, and an attached flexible plastic strip for releasably attaching the sleeve around an individual's arm. Both the sleeve and strip are constructed from a thin—about 0.016 inch thick—sheet of plastic material, such as polyvinyl chloride (PVC), the surfaces of which are inherently self-adhering when cured to thereby cause overlying surfaces of the sleeve and strip to cling together against shearing forces when the cuff is wrapped around an individual's arm and the sleeve is pressurized through the attached pressurizing tube. Adhesive tape is fastened to the free end of the strip to stick the free end of the strip down and keep the strip and sleeve from unwrapping after the cuff is wrapped around an individual's arm and is pressurized, the retention of the pressurized sleeve being, however, due to the inherently self-adhering property of the strip and sleeve.

11 Claims, 2 Drawing Sheets

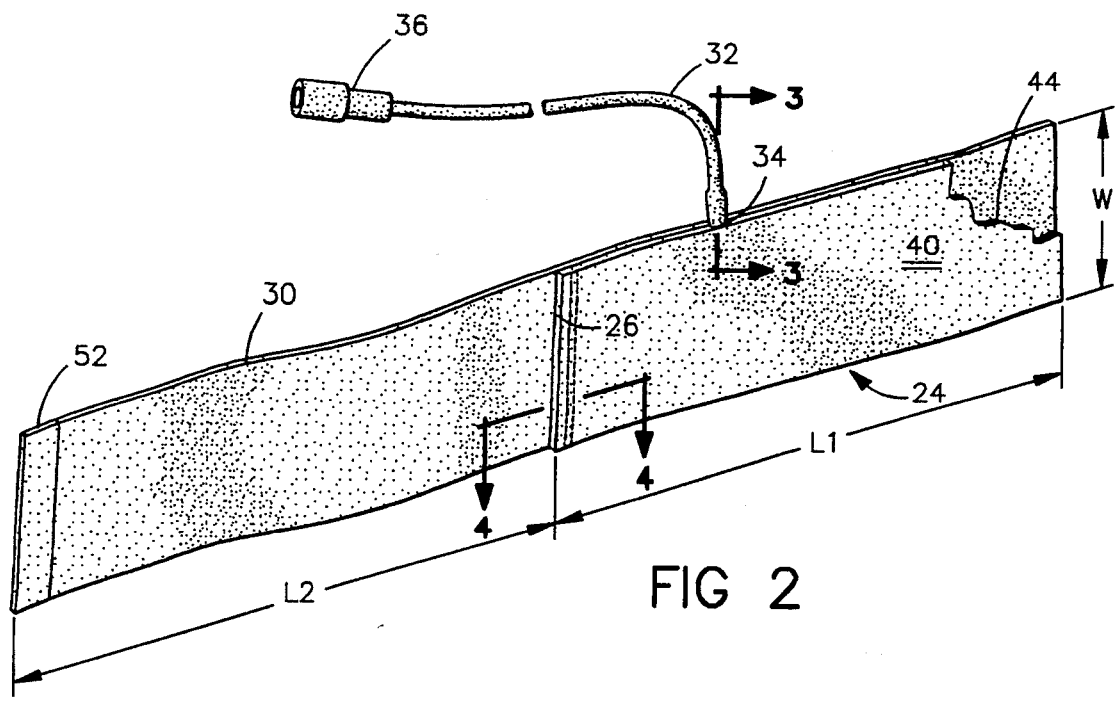
FIG 2
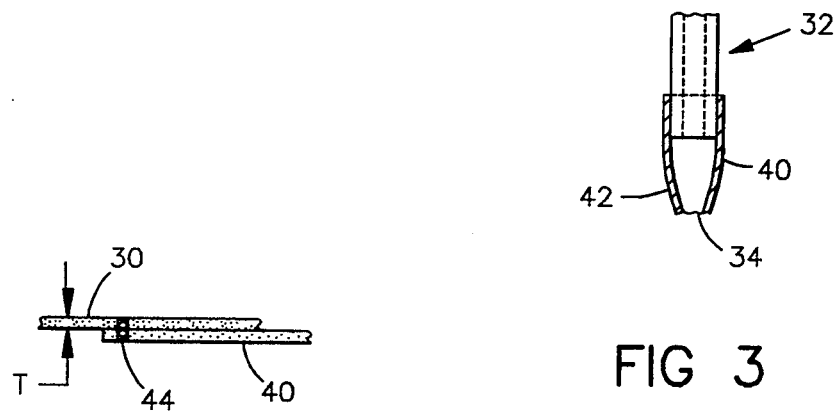
FIG 3
FIG 4

DISPOSABLE PRESSURE CUFF FOR A BLOOD PRESSURE MONITOR

BACKGROUND OF THE INVENTION:

1. Field of the Invention

The present invention relates generally to the field of medical apparatus, more particularly to blood pressure measuring and monitoring apparatus (sphygmomanometers), and still more particularly to pressure cuffs used with and/or are part of such blood pressure measuring and monitoring apparatus.

2. Background Discussion

Virtually every adult and even many children, at least in the United States, have had their blood pressure measured or monitored by the use of a blood pressure measuring and monitoring apparatus, such apparatus being called, in the medical profession, sphygmomanometers. Next to the taking of patients' or individuals' temperatures, the taking of blood pressure is probably the most common medical procedure, and is, in fact, often monitored in homes by individuals or their family members when the individuals suffer from such diseases as high blood pressure (often called hypertension).

Since an individual's blood pressure reading is ordinarily a quick indicator of the individual's condition, the taking of an injured or sick person's blood pressure is generally the first or one of the first medical procedures taken at the seen of an accident or the hospital, even when the individual's injury or illness does not seem to be severe. For instance, a low blood pressure reading may indicate unseen injuries and/or the onset of shock or heart problems, and high blood pressure may warn of a possible stroke. Accordingly, all paramedics and other emergency personnel are virtually always provided with blood pressure measuring and monitoring apparatus.

Blood pressure measuring and monitoring apparatus—sphygmomanometers—commonly used by paramedics and medical personnel consist of an inflatable, flexible sleeve, typically called a cuff, that is wrapped around a patient's arm, ordinarily above the elbow. A small, bulb-type hand pump is connected to the sleeve by a flexible air tube to enable the cuff to be inflated sufficiently to temporarily cut off blood flow in the arm beyond (below) the cuff. A common stethoscope is used to listen to the sound of blood flow in the patient's arm, the sound pick-up end of the stethoscope being positioned under lower regions of the cuff and over an artery in the patient's arm. Connected to the cuff, ordinarily through the hand pump, is a pressure indicating device, such as a mercury manometer or pressure gauge. The hand pump is used to pressurize the cuff until the flow of blood is cut off in the patient's arm; pressure is then slowly released from the cuff and the pressure at which the first sound of resumed blood flow (as determined by the stethoscope) is noted or recorded as the patient's systolic blood pressure. Pressure in the cuff is further reduced and the pressure at which the blood sounds first disappear is noted or recorded as the patient's diastolic blood pressure. To trained individuals, the measured systolic and diastolic blood pressures, ordinarily expressed as the systolic pressure over the diastolic pressure, are very revealing of the patient's condition and may indicate the need for life-sustaining treatment.

As stated above, virtually all injured individuals, whether injured in a vehicle or other accident, or a victim of a shooting, stabbing or beating, have their blood pressure immediately measured and/or monitored by medical personnel, often or usually paramedics, first arriving on the injury scene.

Often the injured individual or individuals whose blood pressure or pressures need to be taken are injured to the extent that some or even profuse bleeding may be occurring or may have occurred, and the individuals' arms about which the blood pressure cuffs have to be installed are bloody. With the ever-increasing prevalence of the AIDS virus (and other blood-borne, infectious diseases, such as hepatitis) in the population, exposure of one person to the blood of an injured or wounded person is a serious risk, especially considering the deadly nature of the AIDS virus.

Consequently, the presence of blood on injured individuals consequently poses a health hazard not only to paramedics and other health professionals treating injured or wounded individuals, but also to other injured or wounded individuals who have to be treated at the same scene of the accident or injury, for example, in the case of automobile accidents injuring more than one person, or shootings injuring more than one person.

The risk of AIDS infection from contact with the blood of individuals carrying the disease may be especially high in some inner-city regions where the incidence of prostitution is great and/or IV drug use is common—both of which are known to carry high incidence of AIDS and both of which tend to result in increased violence which leads to serious, bloody injuries, such as gun-shot and stabbing wounds.

It can, of course, be seen, for example, from television news programs, that medical personnel, such as paramedics, working on individuals that have open wounds where contact with the patients blood is likely or possible, wear disposable surgical gloves to protect their hands. In some instances, such medical personnel also wear partial face masks to prevent the inhalation or ingestion (through an open mouth) of blood or blood mist from an injured patient.

There is, however, the further interest, even in emergency situations, in protecting one injured individual from being contaminated by the blood of another injured individual. For example, paramedics may change their surgical gloves after handling one patient and before handling another patient. In addition, certain instruments, such as scalpels, may be set aside for sterilization and sterilized instruments used for a next patient.

One, possibly unrecognized, source for potentially contaminating one injured individual with the blood of another individual, in the case of open wounds, is the reuse of a blood pressure cuff that has come into contact with a first injured individual's blood. Since blood pressure cuffs are typically constructed of a rubberized fabric they are not subject to sterilization, at least in such emergency situations as an accident or disaster. Moreover, such blood pressure cuffs have heretofore, so far as is known to the present inventor, been too costly to be disposable after a single use.

Accordingly, there has now been invented an inexpensive, but effective, blood pressure cuff that can be disposable after a single use, and the risk of contaminating one individual by the blood of a previous patient, by using a contaminated blood pressure cuff, can thereby be eliminated. Moreover, such disposable blood pressure cuffs can be made sufficiently inexpensive that they may be routinely used and disposed of after a single use even in doctors' offices and hospitals where the risk of subsequent infection by the use of a blood-contaminated blood pressure cuff is ordinarily much less than in emergency accident or disaster scenes or in emergency hospital rooms. The use of such disposable blood pressure cuffs, even in non-emergency situations or where bleeding is present, provides an additional safety factor against the transmission of blood-borne diseases and protects not only patients on which the cuffs are used, but also protects doctors, nurses and hospitals against certain liabilities.

SUMMARY OF THE INVENTION

In accordance with the present invention, there is provided a disposable blood pressure cuff for use in a conventional blood pressure measuring and/or monitoring system. The cuff comprises an elongate, flexible, inflatable plastic sleeve sized to wrap around an individual's upper arm above the elbow, tubing means connected to the sleeve to enable the internal pressurization thereof, and means for releasably attaching the sleeve around an individual's arm.

It is preferred that the sleeve is constructed of a plastic material that is inherently self-adhering so as to cause the outer surfaces of the sleeve to cling to one another against shearing action when the sleeve is wrapped around an individual's arm and the sleeve overlaps itself. The means for releasably attaching the sleeve around an individual's arm includes an elongate strip of plastic material similar to the type of plastic material used for the sleeve and which is connected to the sleeve, the strip tending to cling to itself when the sleeve and the strip are wrapped around an individual's arm so as to hold the sleeve in place when the sleeve is inflated through the tubing means. The strip has a proximal end region that is connected to one end region of the sleeve and, the distal end region of the strip being free. Preferably, the means for releasably attaching the sleeve around an individual's arm further comprises an adhesive region at the distal end region of the strip. In an embodiment, the adhesive region comprises a detachable strip of adhesive tape.

Also preferably, the sleeve and connected strip are formed of polyvinyl chloride which has a thickness of about 0.016 inches.

In use, the sleeve and strip are wrapped around an individual's upper arm, above the elbow, in the same manner as conventional blood pressure cuffs, the inherently self-adhering property of the plastic causing the sleeve and strip to cling to one another where they overlap, with the adhesive strip sticking down the free end of the sleeve to underlying surface regions of the strip sleeve. The inherently self-adhering property of the material permits the sleeve to be inflated in the manner of a conventional cuff without the need for buckles of VELCRO to keep the sleeve from loosening as it is inflated. The cuff is thus inexpensive to construct so as to be disposable after a single use.

BRIEF DESCRIPTION OF THE DRAWINGS

The present invention can be more readily understood by a consideration of the following detailed description when taken in conjunction with the accompanying drawings, in which:

FIG. 2 is a partially cut-away perspective drawing of the disposable, inflatable blood pressure cuff depicted in FIG. 1, showing the cuff in its unwrapped condition and showing as part of the cuff a pressure tubing;

FIG. 3 is a cross sectional drawing taken along line 3—3 of FIG. 2, showing the manner in which the pressure tubing is inserted into the cuff; and FIG. 4 is a cross sectional drawing taken along line 4—4 of FIG. 2, showing the envelope-type construction of the cuff.

In the various FIGS. identical elements and features are given the same reference number.

DETAILED DESCRIPTION OF THE INVENTION

Figure 1:
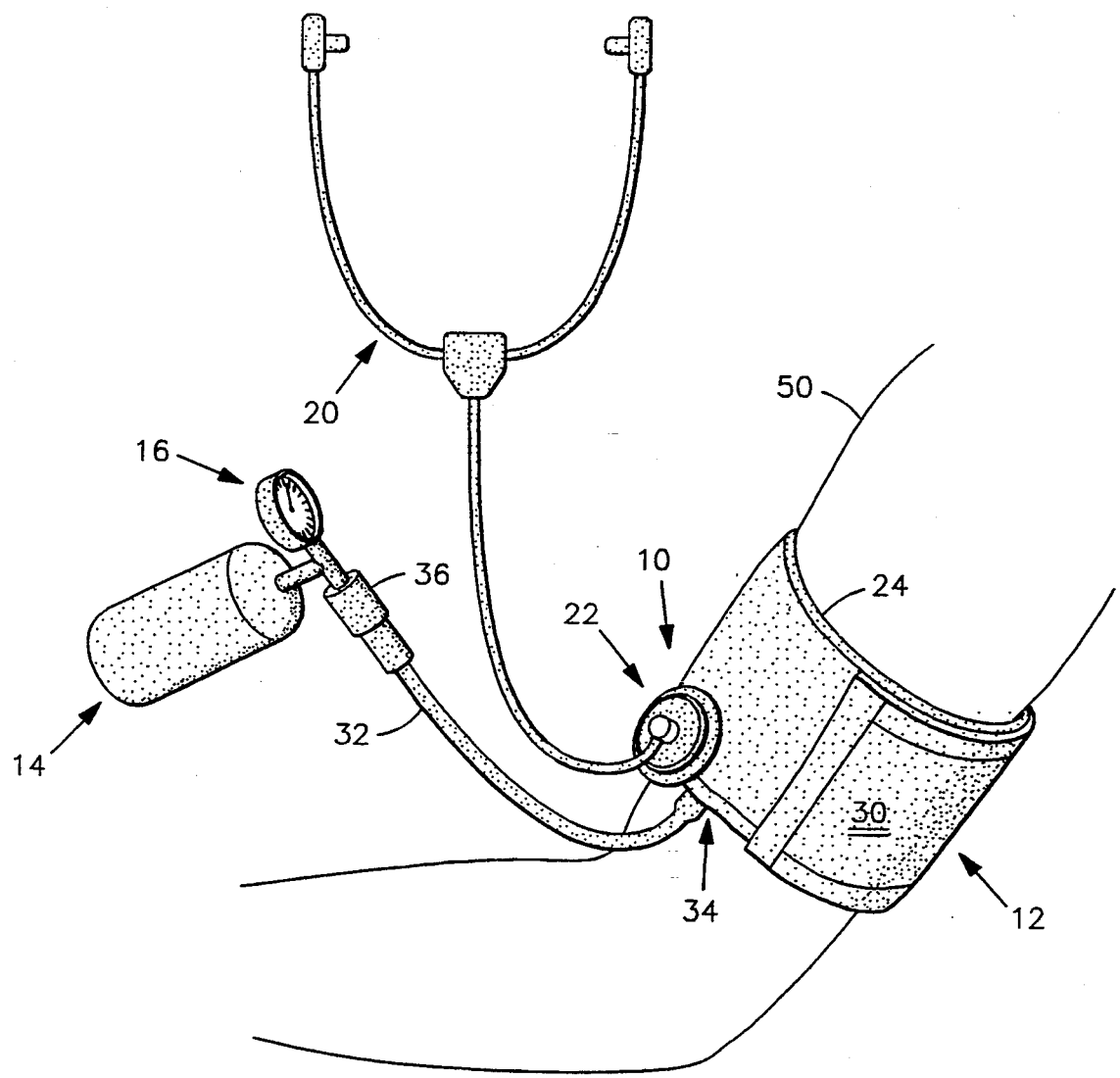
FIG. 1 is a perspective drawing showing the use of a disposable, inflatable blood pressure cuff of the present invention in conjunction with a blood pressure measuring and/or monitoring system, the cuff being shown disposed around a patient's upper arm in a conventional blood pressure cuff position.

There is shown in FIG. 1 a blood pressure measuring and monitoring system 10 which comprises an inexpensive plastic inflatable cuff 12 in accordance with the present invention. Other parts of system include a hand-operated air bulb assembly 14 which is connected to a measuring device 16, for example, a dial pressure gage. Used in conjunction with and, in effect, forming part of system 10 is a conventional stethoscope 20 having a listening end 22 that is shown positioned on an individual's arm 50 beneath lower regions of cuff 12. Neither bulb assembly 14, measuring device 16 nor stethoscope 20 form a part of the present invention, which is specifically directed to cuff 12.

Comprising cuff 12 are a flexible, inflatable plastic sleeve 24 longitudinally connected to a proximal end region L1 of a flexible plastic strip 30 (FIG. 2). Further comprising cuff 12 is a pressure tube 32 having one end 34 extending to the inside of sleeve 24, the other end of the tube having connected thereto a fitting 36 into which pressurizing bulb assembly 14 is detachably received.

Sleeve 24 is preferably constructed from a first and second rectangular sheets 30 and 40 of a thin, flexible plastic material. These sheets 30 and 40 are sealed together around all four edges, for example, by thermal bonding, to form a continuous seal 44 around sleeve 24 (FIG.4). Seal 44 makes sleeve air tight and capable of being inflated through pressurizing tube 32. As shown in FIG. 3, end 34 of pressurizing tube 32, extends between sheets 30 and 40 and is sealed in place when seal 44 is formed.

The length, L1, of sleeve 24 when assembled in the above-described manner is preferably about 12 inches, and its width, W, is preferably about 5 to 5½ inches (FIG. 2). The length, L2, of strip 30 is preferably about 18 inches and it is preferably about the same width as sleeve 28. Alternatively, sleeve 24 may be formed of separate rectangular sheets of flexible plastic that is connected to strip 30 during its sealing operation. The flexible plastic material from which sheets 30 and 40 are constructed, preferably have a thickness, t, of about 0.016 inches (FIG. 4).

An important feature of cuff 12 is that sheets 30 and 40 are constructed of a plastic material, such as polyvinyl chloride (PVC), that a has a surface inherent adhesion quality even when fully cured (polymerized). This inherent adhesion quality causes overlying surfaces of sleeve 24 and strip 30 to cling, or somewhat stick, together against the shearing action caused when cuff 12 is wrapped around an individual's arm 50 and sleeve 24 is inflated for the measuring or monitoring of the individual's blood pressure. Thus, cuff 12 does not require the usual buckle or VELCRO tabs to hold it wrapped around arm 50 and its cost is accordingly reduced.

An inexpensive, transverse adhesive strip 52 (FIGS. 1 and 2) is preferably provided at the free end of strip 32 to keep the strip from unintentional unwrapping after the installation of cuff 12 around arm 50, that is, to keep the free end of the strip in contact with the underlying surface of the strip so that the inherent adhesion quality of the strip and sleeve 24 can be fully effective in keeping cuff 12 on the arm during inflation. It is emphasized, however, that adhesive strip 52, which may simply comprise a strip of common adhesive tape or may alternatively consist of a region of adhesive material applied to strip 32 at its free end, does not function to keep cuff 12 tight around arm 50 when the cuff is inflated—that function is provided by the inherent adhesion quality of surface regions of sleeve 24 and strip 32, as above described.

In the manner described above, cuff 12 is constructed to be inexpensive, yet effective, and can be economically disposed of after a single use, as is intended.

Although there have been described and illustrated a disposable, inflatable blood pressure cuff in accordance with the present invention for purposes of illustrating the manner in which the invention may be used to advantage, it is to be appreciated that the invention is not limited thereto. Therefore, any and all variations and modifications that may occur to those skilled in the applicable art are to be considered as being within the scope and spirit of the claims as appended hereto.

What is claimed is:

1. A disposable blood pressure cuff for use in a conventional blood pressure measuring and/or monitoring system, said cuff comprising:
    a. an elongate, flexible, inflatable plastic sleeve sized to wrap around an individual's upper arm above the elbow, said sleeve being constructed of a plastic material that is inherently tacky so as to cause outer surfaces of said sleeve to cling to one another against shearing action when the sleeve is wrapped around an individual's arm and the sleeve overlaps itself;
    b. tubing means connected to said sleeve to enable internal pressurization thereof; and
    c. an elongate strip of flexible plastic material to the type of plastic material used for the sleeve, said strip being attached to said sleeve and overlapping regions clinging together when the sleeve and the strip are wrapped around an individual's arm so as to hold the sleeve in place when the sleeve is inflated through the tubing means.

2. The disposable blood pressure cuff as claimed in claim 1, wherein said strip has a proximal end region that is attached to an end region of the sleeve and wherein a distal end region of said strip is free.

3. The disposable blood pressure cuff as claimed in claim 2, further comprising an adhesive region at the distal end region of said strip so as to keep said distal end region against an underlying region of said strip so as to keep said strip from unwrapping and assure that the clinging characteristics of the plastic retain the cuff on the individual's arm.

4. The disposable blood pressure cuff as claimed in claim 3, wherein said adhesive region comprises a detachable strip of adhesive tape.

5. The disposable blood pressure cuff as claimed in claim 1, wherein the sleeve is constructed of polyvinyl chloride.

6. The disposable blood pressure cuff as claimed in claim 5, wherein said sleeve has a side-wall thickness of about 0.016 inches.

7. A disposable blood pressure cuff for use in a conventional blood pressure measuring and/or monitoring system, said cuff comprising:
    a. an elongate, flexible, inflatable plastic sleeve sized to wrap around an individual's upper arm above the elbow, said sleeve being constructed of a inherently tacky polyvinyl chloride plastic material so as to cause outer surfaces of said sleeve to cling to one another against shearing action when the sleeve is wrapped around an individual's arm and the sleeve overlaps itself;
    b. tubing means connected to said sleeve to enable internal pressurization thereof; and
    c. an elongate strip of flexible plastic material of the type of plastic material used for the sleeve, said strip having a proximal end region and a distal end region, said proximal end region being attached to one end of said sleeve and said distal end region terminating end a free distal end, said strip tending to cling to itself when the sleeve and the strip are wrapped around an individual's arm so as to hold the sleeve in place when the sleeve is inflated through the tubing means.

8. The disposable blood pressure cuff as claimed in claim 7, including an adhesive strip at the distal end region of the strip to thereby enable the distal end region of the strip to adhere to a underlaying surface of the strip when the sleeve and strip are wrapped around an individual's arm.

9. The disposable blood pressure cuff as claimed in claim 7, wherein the sleeve has a sidewall thickness of about 0.016 inches, and is about 12 inches long and at least about 5 inches wide.

10. A disposable blood pressure cuff for use in a conventional blood pressure measuring and/or monitoring system, said cuff comprising:
    a. an elongate, flexible, inflatable plastic sleeve sized to wrap around an individual's upper arm above the elbow, said sleeve being constructed from an inherently tacky polyvinyl chloride plastic having a wall thickness of about 0.016 inches so as to cause outer surfaces of said sleeve to cling to one another against shearing action when the sleeve is wrapped around an individual's arm and the sleeve overlaps itself and the sleeve is pressurized, a distal end region of one side of said sleeve extending axially beyond the other side to thereby form an elongate retaining strip for wrapping around an individuals arm; and
    b. tubing means connected to said sleeve to enable internal pressurization thereof.

11. The disposable blood pressure cuff as claimed in claim 10, including an adhesive strip at the distal end region of said strip, extending one of said sleeve sides for preventing the overlapping regions of said distal end region from unwrapping and to thereby adhere to one another when the sleeve is wrapped around an individual's arm.

* * * * *